(12) United States Patent
Byington et al.

(10) Patent No.: US 7,504,835 B2
(45) Date of Patent: Mar. 17, 2009

(54) ELECTROCHEMICAL IMPEDANCE MEASUREMENT SYSTEM AND METHOD FOR USE THEREOF

(75) Inventors: Carl S. Byington, Pittsford, NY (US);
Matthew J. Watson, State College, PA (US); Ryan C. Brewer, Webster, NY (US)

(73) Assignee: Impact Technologies, LLC, Rochester, NY (US)

( * ) Notice: Subject to any disclaimer, the term of this patent is extended or adjusted under 35 U.S.C. 154(b) by 0 days.

(21) Appl. No.: 11/748,292

(22) Filed: May 14, 2007

(65) Prior Publication Data
US 2008/0054914 A1    Mar. 6, 2008

Related U.S. Application Data

(63) Continuation of application No. 10/987,069, filed on Nov. 12, 2004, now Pat. No. 7,239,155.

(60) Provisional application No. 60/520,521, filed on Nov. 14, 2003.

(51) Int. Cl.
*G01R 27/08* (2006.01)
*G01N 27/02* (2006.01)
*G01N 27/72* (2006.01)

(52) U.S. Cl. .................. 324/693; 324/698; 73/53.01; 73/53.04

(58) Field of Classification Search ............. 324/693, 324/698; 73/53.04
See application file for complete search history.

(56) References Cited

U.S. PATENT DOCUMENTS

| | | | |
|---|---|---|---|
| 4,198,078 A | 4/1980 | Herbert | |
| 4,646,070 A | 2/1987 | Yasuhara et al. | |
| RE33,789 E | 1/1992 | Stevenson | |
| 5,274,335 A | 12/1993 | Wang et al. | |
| 5,345,182 A | 9/1994 | Wakamatsu | |
| 5,435,170 A | 7/1995 | Voelker et al. | |

(Continued)

FOREIGN PATENT DOCUMENTS

EP        0527176        4/1991

(Continued)

OTHER PUBLICATIONS

Brown, R.W.; Cheng, Y.N.; Chunko, J.D.; Condit, W.C.; Novel Sensors for Portable Oil Analyzers; Wayne A. Bush and Margaret A. Zelina, PREDICT, 9555 Rockside Rd., Cleveland OH 44125; 11980624 080.

(Continued)

*Primary Examiner*—Vincent Q Nguyen
*Assistant Examiner*—John Zhu
(74) *Attorney, Agent, or Firm*—Duane C. Basch; Basch & Nickerson LLP

(57) ABSTRACT

Disclosed is a method and apparatus for an electrochemical impedance measurement, and in particular circuitry and components employed for such measurements. The system employs an injected broadband AC signal to produce an associated response signal. The subsequent analysis of injected and response signals, considering both magnitude and phase, gives broadband impedance and therefore fluid characteristic information. An embodiment described is relative to a smart oil sensor system suitable for sensing, analyzing and reporting the condition of oil or other liquids used in equipment and machinery.

22 Claims, 6 Drawing Sheets

U.S. PATENT DOCUMENTS

| | | |
|---|---|---|
| 5,777,210 A | 7/1998 | Voelker et al. |
| 5,789,665 A | 8/1998 | Voelker et al. |
| 5,793,196 A | 8/1998 | White |
| 5,889,200 A | 3/1999 | Centers et al. |
| 5,995,914 A | 11/1999 | Cabot |
| 6,028,433 A | 2/2000 | Cheiky-Zelina et al. |
| 6,147,497 A | 11/2000 | Berryman et al. |
| 6,223,589 B1 | 5/2001 | Dickert et al. |
| 6,253,601 B1 | 7/2001 | Wang et al. |
| 6,459,995 B1 | 10/2002 | Collister |
| 6,535,001 B1 | 3/2003 | Wang |
| 6,577,112 B2 | 6/2003 | Lvovich et al. |
| 6,583,631 B2 | 6/2003 | Park et al. |
| 6,620,186 B2 | 9/2003 | Saphon et al. |
| 6,666,968 B2 | 12/2003 | Smith et al. |
| 6,718,819 B2 | 4/2004 | Schoess |
| 6,741,938 B2 | 5/2004 | Berndorfer |
| 6,812,716 B2 | 11/2004 | Fawcett |
| 6,859,049 B2 | 2/2005 | Khatchatrian et al. |
| 6,937,332 B2 | 8/2005 | Engler et al. |
| 7,239,155 B2 | 7/2007 | Byington et al. |
| 7,328,604 B2 | 2/2008 | DeNatale et al. |
| 2002/0189367 A1 | 12/2002 | Gomm et al. |
| 2003/0046985 A1 | 3/2003 | Schoess |
| 2005/0058510 A1 | 3/2005 | Parker |
| 2006/0020427 A1 | 1/2006 | Kahn et al. |
| 2006/0243032 A1 | 11/2006 | Liu et al. |
| 2007/0074563 A1 | 4/2007 | Liu et al. |

FOREIGN PATENT DOCUMENTS

| | | |
|---|---|---|
| GB | 2029586 | 3/1980 |

OTHER PUBLICATIONS

Saba, C.S.; Wolf, J.D.; Tandem Technique for Fluid Testing; University of Dayton Research Institute, Dayton, OH 45469; Phillip W. Centers, Wright Laboratory USAF, WPAFB, OH 45433; 1998.

International Search Report and Written Opinion dated Sep. 5, 2008 for PCT/US08/62883.

ELECTROCHEMICAL IMPEDANCE MEASUREMENT SYSTEM AND METHOD FOR USE THEREOF

PRIORITY CLAIM

This application is a continuation of U.S. application Ser. No. 10/987,069 for an "ELECTROCHEMICAL IMPEDANCE MEASUREMENT SYSTEM AND METHOD FOR USE THEREOF" filed Nov. 12, 2004 by C. Byington et al. and priority is hereby claimed from application Ser. No. 10/987,069 as well as from Provisional Application No. 60/520,521, for a "Smart Oil Sensor System And Method For Use Thereof," filed Nov. 14, 2003; both applications being assigned to Impact Technologies, LLC, and also hereby incorporated by reference in their entirety.

GOVERNMENT LICENSE RIGHTS

Aspects of this invention were made with Government support under SBIR Contract Number: N00014-02-M-0178, awarded by the Office of Naval Research. The U.S. Government may have certain license rights in aspects of this invention.

This invention relates generally to fluid analysis, and more particularly to a sensing system suitable for measuring the broadband impedance of oil, or other fluids used in or with equipment, machinery and the like. This measurement could be used, for example, to extract evidence or features for analyzing the condition or composition of such fluids.

BACKGROUND AND SUMMARY

Electrical and electrochemical properties, such as conductivity and dielectric constant, are often used to assess the condition of oil and other fluids. These measurements have traditionally limited the response of the measurement to specific frequencies only and therefore do not consider the overall spectrum response of the system. Additionally, the measurement is typically accomplished using one or more fixed-amplitude, single frequency tones. In most cases, the magnitude of the response is used as the sole gauge. The phase change of the response, which contains information needed to evaluate capacitance and inductance changes, is rarely used in field applications. For example, U.S. Pat. Nos. 4,646,070 (Yasuhara) and 6,028,433 (Cheiky-Zelina) disclose designs in which only one frequency tone is evaluated. U.S. Pat. No. 6,583,631 (Park) presents a method of determining only capacitance. Similarly, U.S. Pat. No. 6,535,001 presents a capacitive sensor that outputs a single DC voltage level, while U.S. Pat. No. 6,459,995 relies on a fixed frequency tone of an LC oscillator circuit to produce the interrogation signal. These designs provide little information about the full electrochemical response of the fluid. Furthermore, these methods neglect useful information that can be extracted from the fluid's broadband impedance. For those systems that do consider a multitude of frequencies, the fluid is repeatedly interrogated by a single frequency waveform, which results in full fluid characterization taking an extended time, up to 50 minutes (as disclosed in U.S. Pat. No. 6,577, 112 by Lvovich). This approach is susceptible to very large errors due to environmental changes that can occur during the interrogation window. U.S. Pat. No. 5,889,200 describes a sensor that interrogates a fluid simultaneously using a multitude of frequencies in the form of a square wave. However, only one measurement (conductivity) is extracted and no effort is made to evaluate the fluid's broadband impedance. A square wave is also inferior to the interrogation signal presented by the current invention in the inability to control the signal's amplitude at specific frequencies. A similar design presented in U.S. Pat. No. 5,274,335, employs a triangle wave for interrogation, which suffers the same drawbacks as the square wave interrogation signal.

In most cases, the failure mechanism that dominates a mechanical system can be traced back to the fluid quality degradation or contamination of the system. It is precisely for this reason that on-line, in situ oil quality analysis is the key building block to effective diagnostics and prognostics for mechanical systems. The present invention directly addresses, this need in addition to the aforementioned technology shortcomings, with a novel sensor package to determine a fluid's broadband electrical impedance, which can be used to, among other things, predict quality and degradation in a range of fluid systems.

One aspect of the present invention is a measurement system comprising: a low-powered, broadband, interrogation signal; the analog circuitry needed to condition and facilitate acquisition of the interrogation (and response) signal(s); a data acquisition device for capturing these signals; and a processor and algorithms to control the interrogation and acquisition process as well as interpret the measurements to determine the impedance of the fluid.

In accordance with another aspect of the present invention, there is provided a method for measuring a fluid's impedance as a response to an interrogation, comprising: injecting a broadband signal containing a range of frequencies (range is dependent upon fluid type); and measuring the response to such signals through a fluid to determine impedance.

As part of this invention, a digital to analog converter is used to generate sensor interrogation waveforms comprising a composite of sinusoidal waveforms of varying frequency. A measurement circuit provides an analog to digital converter with inputs corresponding to the original interrogation signal and the sensor's response to that signal. A processor, in the form of a microcontroller, digital signal processor, a remote computer, etc. performs analysis of the response signals using a set of algorithms designed to calculate the impedance of the fluid based on magnitude and phase measurements extracted from the digitized input signals. In one embodiment, the sensor electrodes are constructed of two conductive plates that allow a representative fluid sample to pass between the plate surfaces. There is no intent to restrict the geometry of the electrodes to solely parallel plate designs; concentric rings, coaxial cylinders, and redundant (multiple version of a given design allowing a redundant measurement) electrodes should also be considered.

The measurement produced by this invention can be processed for the purpose of tracking specific electrochemical properties (conductance, capacitance, dielectric constant, inductance, and derived combinations), which have been demonstrated to be an effective method to sense changes in fluid quality, as indicated by Saba, C. S., and Wolf, J. D., "Tandem Technique for Fluid Testing", Joint Oil Analysis Proceedings, 1998, pp. 81-90; Brown, R. W., et al., Novel Sensors for Portable Oil Analyzers, Joint Oil Analysis Proceedings, 1998, pp. 91-100; and Brown, R. W., and Cheng, Y., "Mathematical Physics Optimization of Electrical Sensors for Contaminant Detection", 7th Annual Users Conference, Las Vegas, Nev., October 1996. However, there is no intent to limit the invention for use in determining oil quality and the application of impedance measurement to other fluids, liquid plastics, and other 2-phase or variance substance problems is implied.

Figure 1A:
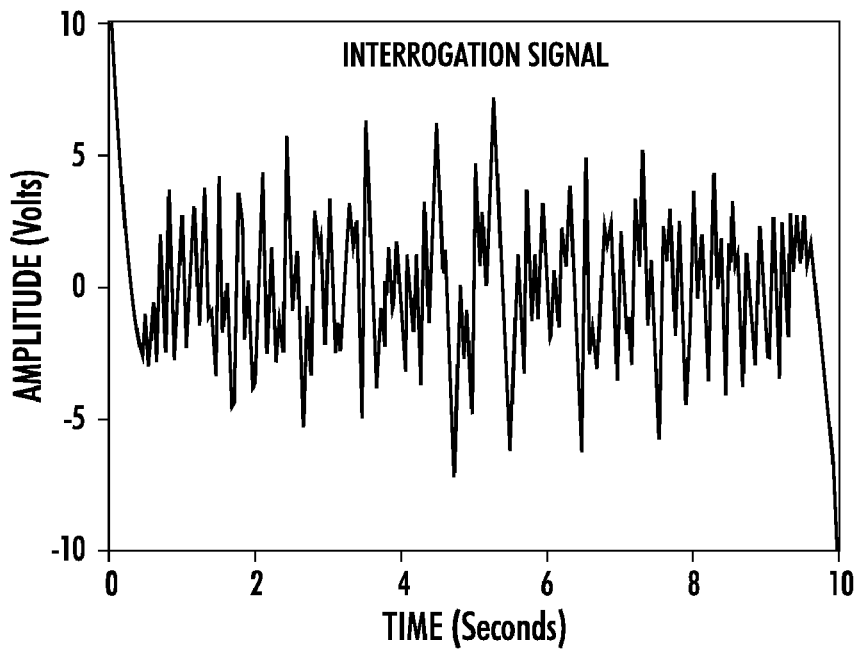
FIGS. 1A and 1B, respectively, show the excitation and response signals of a fluid impedance measurement.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the appended claims.

DETAILED DESCRIPTION

For a general understanding of the present invention, reference is made to the drawings. In the drawings, like reference numerals have been used throughout to designate identical elements.

As opposed to the single tone techniques described above, the concept for taking broadband electrical impedance measurements of a fluid system builds upon AC Voltammetry techniques used in the laboratory for characterization of electrochemical reactions. The basis of this concept involves injecting an alternating current (AC) signal into a system and measuring the system's response at the frequency of the injected signal. The impedance of the system can then be determined by comparing the differences between the interrogation (excitation) signal and the response signal. In the case of a fluid system, measurable levels of current are not possible and a voltage interrogation must therefore be used (as discussed below).

Figure 1B:
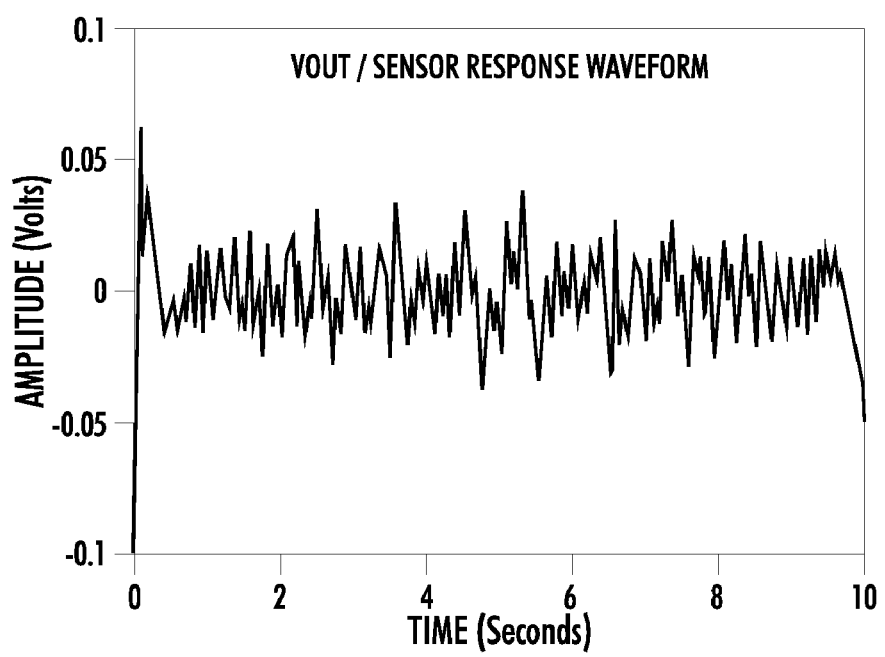

As illustrated in FIG. 1A, a broadband voltage signal is injected into a fluid, versus a single tone, and the broadband response is measured; for example as the signal depicted in FIG. 1B. This broadband approach provides an assessment of impedance over a wide range of frequencies and therefore better captures the total impedance response of the system. Moreover, the approach uses both magnitude and phase changes (complex impedance) in its assessment of impedance. The complex impedance signal better reflects the actual impedance of the fluid by accounting for inductive and capacitive changes in the fluid as opposed to a simple resistance measurement, and therefore provides a significantly more robust measurement. It will be further appreciated that although the instant disclosure is directed to fluids such as oil, the scope is not limited solely to fluids, but may include gaseous phase materials as well—particularly materials that undergo phase transformations. Accordingly, the term fluid, as used herein, is intended to encompass liquids and gasses.

The broadband interrogation signal depicted in FIG. 1A may be created by combining discrete waveforms to create a broadband, composite signal. In one embodiment, the signal of FIG. 1A is created via firmware in an embedded processor which interfaces a digital to analog converter. By interrogating the impedance sensor with this unique composite signal, a significant time savings is achieved as compared tone-at-a-time methods. Typical frequencies used in the interrogation signal range between DC and 10 kHz. The specific frequencies used for interrogation vary depending on the impedance of the fluid to be measured in its normal, uncontaminated state. For example, for diesel oil, utilizing frequencies from 1 Hz to 1 kHz will lead to impedance curves similar to that shown in FIG. 2B.

Figure 2A:
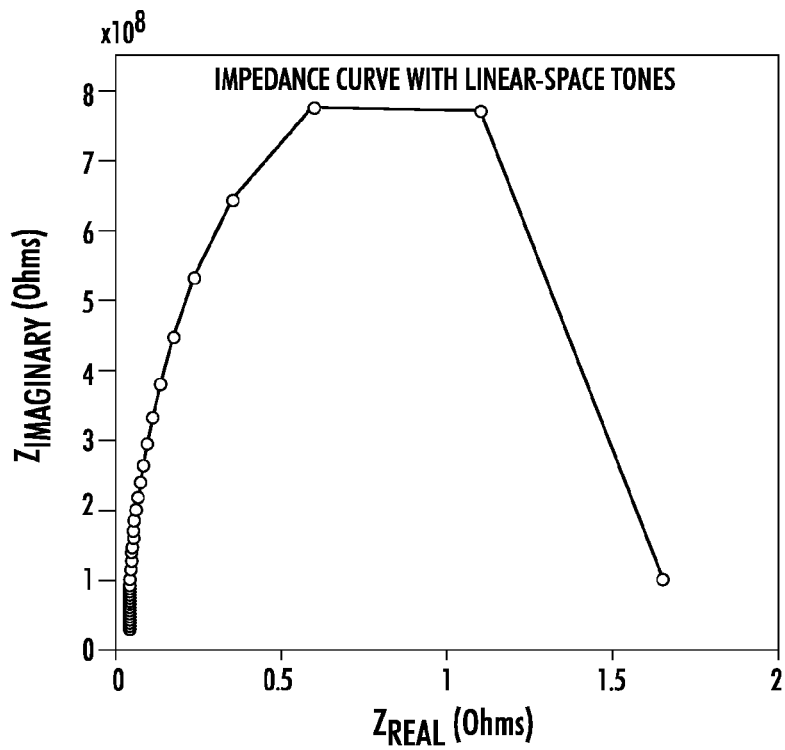
FIGS. 2A and 2B are illustrative comparisons of impedance curves generated using linear-spaced tones versus log-spaced tones, respectively.
Figure 2B:
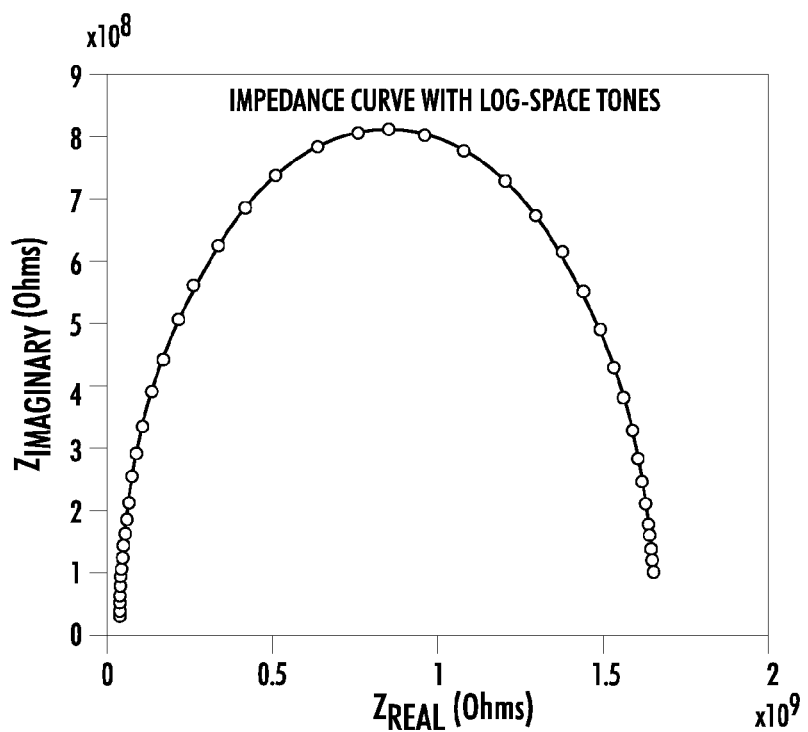

Frequencies are selected such that they are logarithmically spaced over the selected range of frequencies. By logarithmically spacing the frequency points used in the interrogation signal, the frequency range can be maximized while the number of discrete tones used is minimized. Equation 1 is used for generating a series of logarithmically spaced frequency values for a given decade defined by D.

$$f_D(n) = 10^{(D + \frac{n}{N-1})} \text{ for } n = 0, 1, 2, \ldots, N-1 \quad (1)$$

where N is the desired number of frequency points and D is the desired decade the frequencies should span. The importance of using logarithmically spaced points is illustrated in FIGS. 2A and 2B. The figures depict the measured impedance, represented on a Nyquist plot, that results from using linearly spaced frequencies (FIG. 2A) versus logarithmically spaced frequencies (FIG. 2B). Although the figure generated using linear-spaced tones contains twice the number of tones as the figure generated using log-spaced tones, the impedance curve resolution is still very poor at low frequencies (right side of curve). Therefore, by employing an interrogation signal with log-spaced tones, fewer tones can be used to gain a greater amount of impedance information, greatly reducing post acquisition processing requirements.

Due to the nature of capacitive sensor measurements, high frequency interrogation signals generate a stronger signal response than low frequency signals. A method was therefore designed to insure optimum data acquisition system resolution across the entire frequency band. During signal creation, one interrogation signal is created for each decade spanned by the frequency range of interest. The response of the system is assessed for each decade independently and then re-assembled during post-processing. Similar methods such as splitting the waveform by octaves could also be used depending on data acquisition requirements. By substituting Equation 1 into the formula for generating the interrogation signal, wD(t), based on decades becomes $$w_D(t) = A \cdot \sum_{n=0}^{N-1} \sin(2\pi \cdot 10^{(D + \frac{n}{N-1})} \cdot t) \quad (2)$$

where A is a scaling value used to obtain the desired magnitude (i.e. voltage), D defines the decade of frequencies spanned by $w_D(t)$ and N is the number of log-spaced tones. The scaling value, A, is selected such that the full dynamic range of the digital to analog converter, which outputs the interrogation signal, is utilized. This will ensure that the bit resolution of the sampled signal is adequate for performing impedance calculations. As mentioned, D specifies the desired waveform decade; for example, a fluid found to have an optimal interrogation range spanning 1 Hz to 100 Hz would be sampled by 2 waveforms, one including frequencies from 1 Hz to 10 Hz (D=0) and one for 10 Hz to 100 Hz (D=1). This allows the gain settings of the data acquisition system to be adjusted between interrogation signals to achieve high resolution for all frequencies within the composite signals. The length of the time vector, t, is set so that multiple cycles of each tone are injected into to sensor. The total number of cycles needed is determined from the lowest frequency in the decade and the frequency resolution needed to accurately resolve all of the tones in the interrogation waveform when evaluated in the frequency domain.

The general equation for the relationship between impedance, voltage, and current is $$Z = \frac{V}{I} \tag{3}$$

Figure 3:
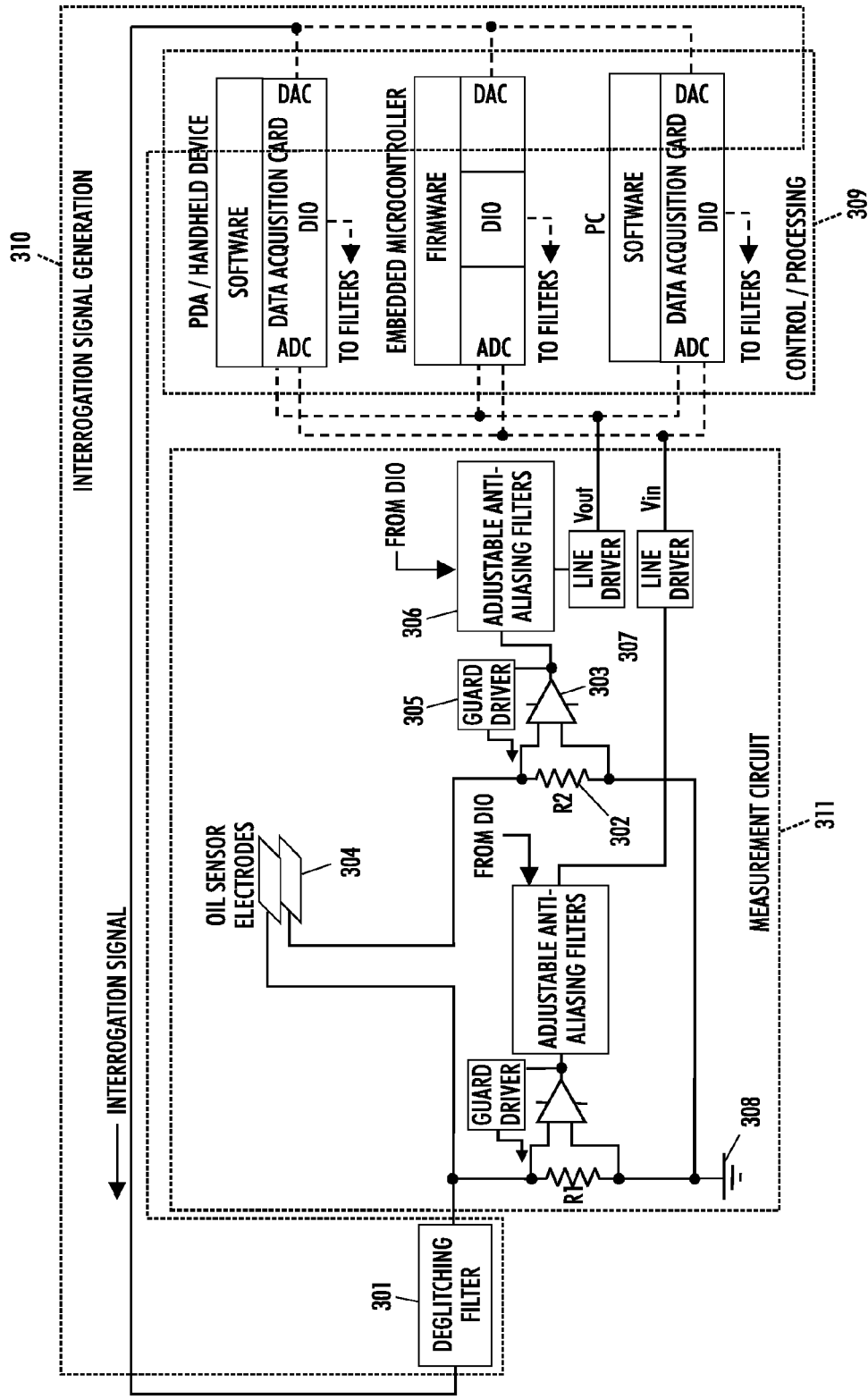
FIG. 3 is a representation of an exemplary fluid sample measurement circuit.

Fluid is a very high impedance medium and, unless special measurement circuitry is applied, measurable levels of current are only achievable at moderate to very high-powered signals. FIG. 3 shows the novel circuit configuration developed for the present invention that allows impedance to be measured with a low-powered signal. For this circuit configuration, power consumption for the interrogation waveform is less than 5 mW, while the complete system (including an embedded microcontroller) power consumption is less than 1W.

Referring to FIG. 3, three primary functional components of the system are represented in the figure. First is a means for generating an interrogation signal 310 for injection into the fluid. As described herein, the interrogation signal is a broadband AC signal created by the circuitry under the control of a pre-programmed or logic based device such as a microcontroller or similar processor. Next, is response measuring means 311, which is intended to receive the response to the injected interrogation signal passed through the fluid and generate the output signal for processing. Lastly, control and processing means 309 are provided so as to enable the analysis of the response signal as further disclosed herein. Regarding an embedded implementation, the processing and control functions of the system can be implemented via a microcontroller, DSP, microprocessor, FPGA, or similar device. For a handheld or PC based embodiment this functionality is performed via software running on the host system's processor and communicated via a data acquisition card.

The configuration shown in FIG. 3 treats the oil sensor 304 as a transmission channel for the input AC signal. Thus, the input and output signals have the same reference ground 308, and by analysis of two voltage measurements the sample fluid's impedance can be calculated. Due to the strong relationship between oil impedance and temperature, from an electrochemical impedance measurement perspective, a temperature measurement adds significant value to the calculated impedance. For this reason, while not shown in FIG. 3, the measurement circuit also incorporates a temperature measuring device that is placed in (or very near) the sample fluid. This device is in the form of a thermistor, thermocouple, or like device.

A digital to analog converter (DAC) is used to generate the composite waveforms that are injected into the oil sample. Such a DAC is included in a multipurpose microcontroller sold as part number C8051F040, by Silicon Laboratories. A deglitching/reconstruction filter 301 is used to smooth errors in the output of the digital to analog converter, providing a more accurate representation of the intended interrogation waveform and removing high frequency errors.

Due to the very high impedance of oil, selection of R2 (302) and the instrumentation amplifiers 303 is critical to the operation of the circuit. R2 is selected to have high resistance, known frequency response, and a low temperature coefficient. The value of R2 should preferably match the average resistance of the fluid to be measured over the frequency range of interest. In some fluids this value will be very high, necessitating the use of a smaller resistor and a gain stage in the instrumentation amplifier to prevent unacceptable noise levels. The instrumentation amplifiers must have extremely low (preferably less than 100 fA) input bias currents and very high input impedance (preferably greater than 1 GΩ) to avoid large measurement errors. The error that can be created by low input resistance can be calculated by:

$$\text{Error} = 1 - \frac{R_{INPUT}}{R_{MEASURE} + R_{INPUT}} \tag{4}$$

Note, that $R_{MEASURE}$, for the purposes of this disclosure, is equivalent to R2 in FIG. 3. As an example, for diesel oil and like fluids, the highly resistive nature of the fluid makes a value of approximately 500 MΩ optimal for R2. However, if the selected instrumentation amplifier has an input resistance of 1 GΩ, by application of equation 4, the measurement error is 33%. Therefore, by reducing R2 to 5 MΩ, or by increasing the amplifier's input resistance similarly, measurement error is reduced to 0.5%.

In a typical highly resistive fluid like oil, currents through the sensor 304 would be measured in nanoamps. Typical instrumentation amplifiers also have bias currents measured in nanoamps. This can result in measurement errors overwhelming the actual measurement. To counteract this effect, a specialized ultra-low bias current instrumentation amplifier, such as the INA116 manufactured by Texas Instruments, is used in addition to guard rings implemented on the PCB layout to reduce leakage. Guard drivers 305 are also implemented to further reduce leakage currents caused by cable capacitance. By selecting the correct amplifier, and implementing guarding techniques, leakage currents can be reduced to femto-amps.

Due to the unique composite interrogation signal used, which entails separate waveforms for each decade, specially designed anti-aliasing filters 306 are used to limit the bandwidth of the interrogation (Vin) and response (Vout) signals. Typically, a single anti-aliasing filter is used for each channel of input, but due to the interrogation method used for this design, this would require the analog to digital converter (ADC) to greatly oversample the low frequency waveforms to prevent aliasing. To avoid this situation, multiple anti-aliasing filters are implemented on each channel (Vin and Vout), and one filter is selected for each interrogation waveform via the digital I/O (DIO) lines of the controlling means 309. This implementation can be achieved by using multiple active/passive filter gain stages selectable through an analog switch device, or by using a variable cutoff frequency anti-aliasing filter. By limiting the bandwidth, the sampling rate required to avoid aliasing is reduced, thus reducing the amount of data required to perform accurate frequency spectrum analysis, and furthermore reducing post acquisition processing time.

The data acquisition system can be implemented locally, via an analog to digital converter module or multi-purpose microcontroller with integrated ADCs, or remotely, via a data acquisition system. FIG. 3 shows three possible embodiments of the control and processing circuitry 309 required to perform an impedance measurement. The embedded implementation relies on a microcontroller to interrogate the sensor via a D/A converter (DAC) and sample the response via an A/D converter (ADC) module. The PC implementation comprises a data acquisition card used in conjunction with a set of software to perform post-acquisition analysis. Additionally, a handheld version is shown that also uses a data acquisition card to communicate with the measurement circuit.

Line drivers 307 serve multiple purposes depending on the configuration of the data acquisition system. For A/D converters capable of bipolar inputs, the line driver acts as a simple buffer circuit to reduce the source impedance of the Vout or Vin signal. For implementations utilizing a unipolar A/D converter, this circuit is used to scale and level-shift the voltages in addition to lowing the source impedance.

The measurement path for Vin and Vout is design to be identical for each measurement. This allows for simple calibration routines to be implemented that can eliminate stray circuit effects such as cable capacitance and inductance, propagation delay, phase and magnitude distortions (from filters), and part tolerances. By shorting the conductive plates of the sensor and performing an impedance calculation these effects can be quantified and removed from future measurements. This measurement will be identified as Zsensor in the following equations.

An algorithm has been developed to translate simple voltage measurements, Vin and Vout, into complex impedances. The impedance of the sample fluid can be calculated by an equation, derived from equation 3, as follows:

$$Z_{OIL} = \frac{V_{OIL}}{I_{OIL}} = \frac{V_{IN} - V_{OUT}}{\frac{V_{OUT}}{R}} - Z_{SENSOR} \quad (5)$$

where R is equal to R2 from FIG. 3. This equation can be rewritten to show the effects of phase shift on the interrogation signal:

$$Z_{OIL}(\omega) = \frac{V_{IN}(\omega t) - V_{OUT}(\omega t - \phi)}{V_{OUT}(\omega t - \phi)} \cdot R - Z_{SENSOR} \quad (6)$$

Figure 4:
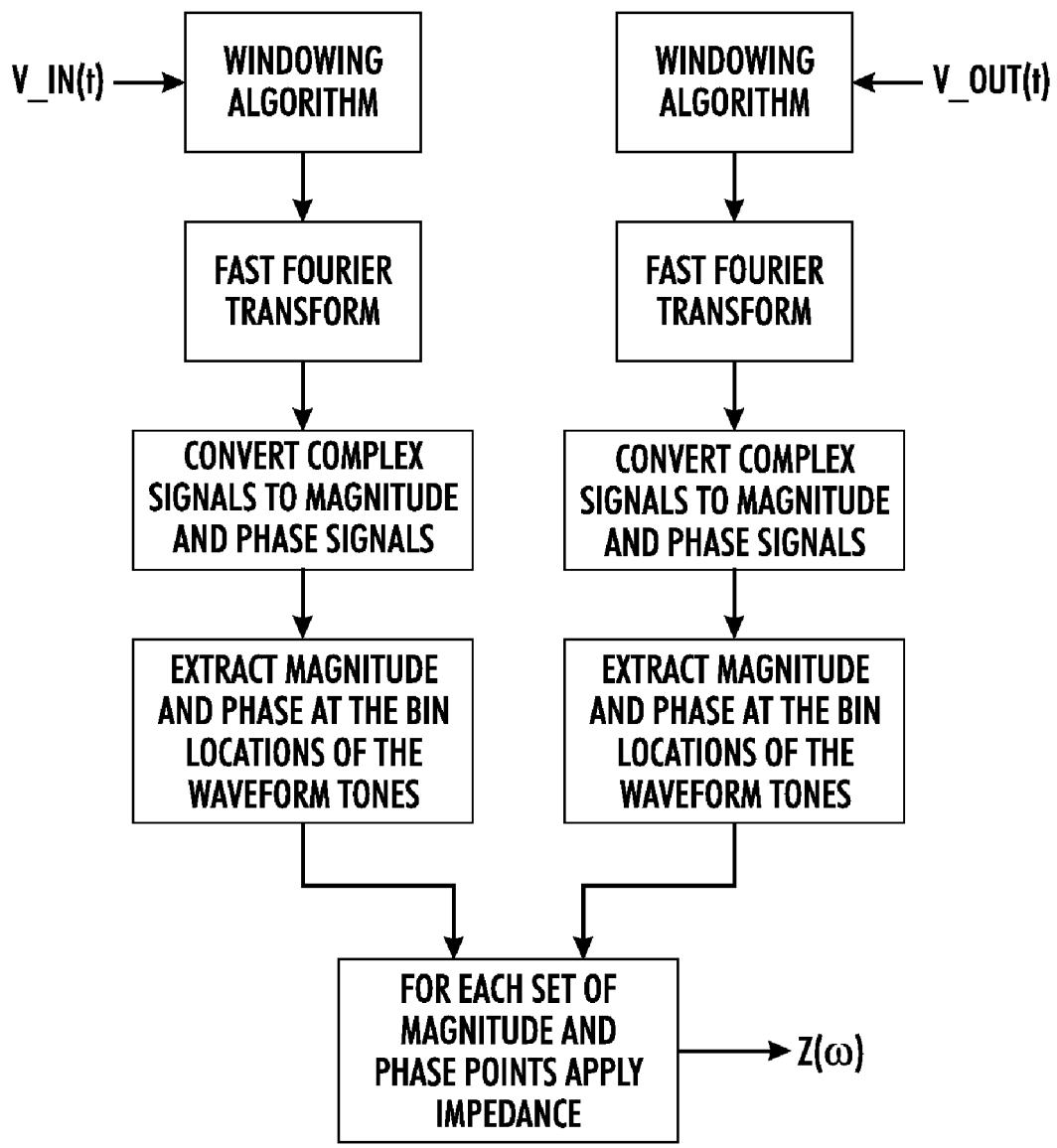
FIG. 4 is a flow chart illustrating a post-processing procedure for calculating impedance values.
Figure 5A:
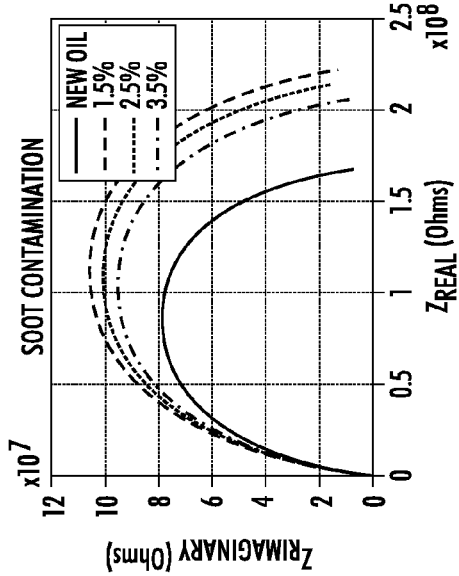
FIGS. 5A-5D are illustrative graphical representations showing the effect of various contaminants on an oil impedance curve.
Figure 5B:
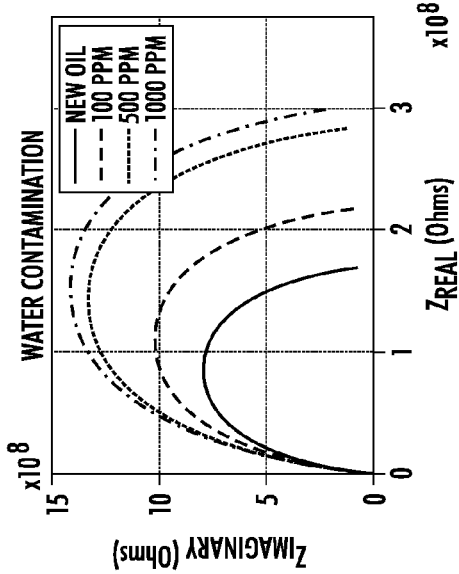
Figure 5C:
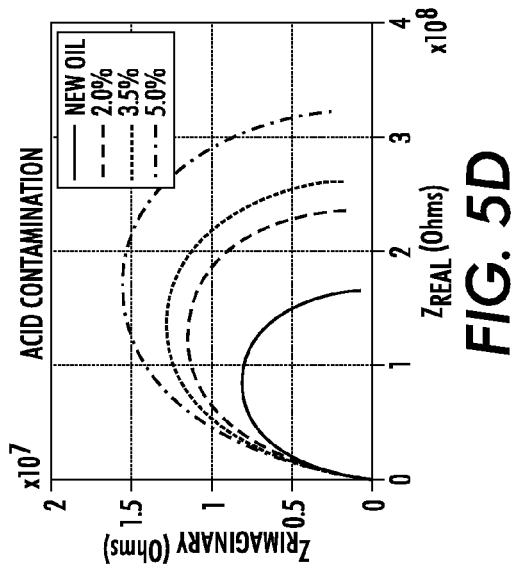
Figure 5D:
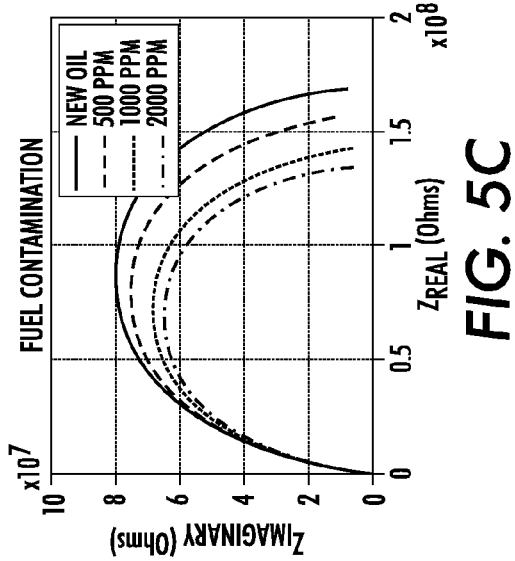

After measuring the input and output signals, VIN and VOUT, and storing the data in a memory, a post-processing algorithm is used to compute the impedance of the oil. This computation is accomplished by determining the change in phase and magnitude of the two signals at each of the frequencies in the excitation waveform. In one embodiment, the phase and magnitude of each signal is found by applying a windowing algorithm (looking only at a portion of the data over a defined timer period), taking the Fast Fourier Transform (FFT) of the two signals, and then locating the peaks in the frequency domain at each of the frequencies of the waveform. As implied by Equation 6, impedance is calculated by determining the change in phase and magnitude of the two signals at each of the frequencies in the excitation waveform. The phase and magnitude of each signal is found by applying a Blackman windowing algorithm, taking the Fast Fourier Transform (FFT) of the two signals, and autonomously locating and extracting magnitude and phase information for frequencies included in the interrogation waveform, $f=\omega/2\pi$. The phase and magnitude signals of the input and output voltages are then converted into complex values, and the impedance of the fluid sample is calculated using Equation 6. This process is also depicted in FIG. 4.

As indicated, the impedance of the fluid sample can be represented on a Nyquist plot, the x and y values of which correspond to the real and imaginary impedance values (respectively) that are obtained by expressing the impedance in rectangular form. By applying Euler's relation, the calculated values can be converted from polar to rectangular form according to Equation 7.

$$Z_{OIL}(\omega) = Ze^{j\phi} = Z(\cos\phi + j\sin\phi) = Z\{re\} + jZ\{im\} \quad (7)$$

Plotting the imaginary impedance versus the real impedance of a diesel oil sample results in a curve similar to that shown in FIG. 2B.

Once an impedance curve is calculated its structure can provide features that are indicative of oil quality. FIGS. 5A-5D show impedance measurements taken at various degradation modes using the method described by this invention. Such a method may include measuring the low-powered, broadband, AC impedance for a plurality of fluid types and generating signals indicative of their impedances; collecting the signals indicative of their impedances; storing the signals indicative of their impedances; and subsequently processing the stored impedance signals to determine at least one characteristic for each of the plurality of fluid types. As can be seen, clear separability and trending is possible for all tested contaminants. By monitoring features of these impedance curves for changes and correlating them against a knowledge base of known oil degradation modes or fluid quality condemning limits, it is possible to determine the remaining useful life of a sample.

Figure 6A:
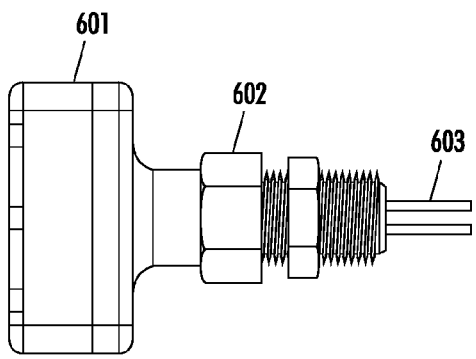
FIGS. 6A-6C show an embodiment of the fluid impedance sensor.
Figure 6B:
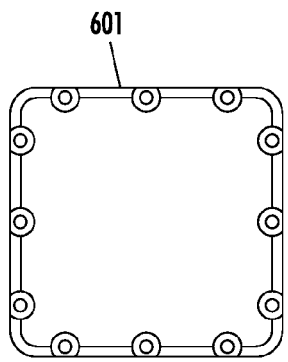
Figure 6C:
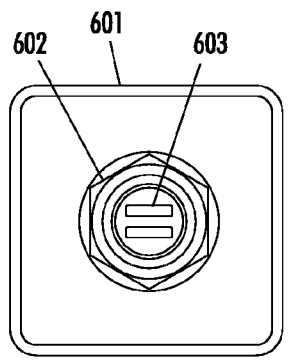

To reduce EMI, a specially designed PCB and enclosure was created for the purposes of this invention. The circuit board is designed with an isolated power supply, sensitive components placed on a single side of the board, and unused portions of the board filled with grounded copper. Due to the small size of this board it can be placed within inches of the sensor electrodes, further reducing the possible effects of EMI. FIG. 6 shows one embodiment of the sensor and electronics housing. The electronics housing 601 is constructed out of a conductive metal or lined with metal shielding to prevent measurement errors caused by the electrically noisy environments the sensor would be used in. A reusable, sealed connector assembly 602 is used to simplify the connection of the electronics housing to the sensor head assembly 603. The sensor head assembly is threaded to allow for easy installation into existing systems via the drain plug or in a fluid system connector for example. As stated previously, there is no intent to limit the size, shape, number, or spacing of the sensor electrodes so long as they are formed of a conductive material such as brass, copper, or stainless steel and are separated by a highly resistive material (e.g. Teflon or other insulators). Other than the parallel plate configuration show in FIG. 6 (603), parallel line/wire, point source to plate, and mixed combinations or variants of these geometries, should be considered.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

What is claimed is:

1. A method for predicting fluid quality and degradation in a fluid system, comprising:

injecting a broadband signal for impedance measurement into the fluid, wherein the broadband signal provides an assessment of impedance over a range of frequencies and where the range of frequencies is at least a decade of frequencies;

measuring a low-powered, broadband, AC impedance for a fluid and generating signals indicative of the impedance;

conducting an analysis of the measured impedance signals to infer a characteristic of the fluid and its constituent components, wherein the analysis further includes
assessing the signals indicative of impedance for each decade independently, and
subsequently re-assembling the signals; and
storing at least one characteristic of the fluid.

2. A method for predicting fluid quality and degradation in a fluid system, comprising:
injecting a broadband signal for impedance measurement into the fluid, wherein the broadband signal provides an assessment of impedance over a range of frequencies and where the range of frequencies is at least a decade of frequencies;
measuring a low-powered, broadband, AC impedance for a the fluid in response to the injected broadband signal and generating output response signals indicative of the measured AC impedance;
conducting an analysis of the measured impedance signals to infer a characteristic of the fluid and its constituent components, wherein the analysis further comprises,
windowing a portion of the injected broadband signal and output response signal for a common time interval,
taking a Fast Fourier Transform of the injected broadband and output response signals, and
using the Fast Fourier Transforms, locating the peaks in the frequency domain at each of the frequencies of the resultant waveform, wherein phase and magnitude signals of the input and output voltages for the injected broadband and output response signals are then converted into complex values and the impedance of the fluid is calculated; and storing at least the impedance of the fluid.

3. A method for sensing electrochemical impedance of a fluid, comprising:
injecting an AC broadband, composite interrogation signal consisting of multiple frequencies overlaid upon each other within a composite waveform into the fluid;
simultaneously measuring both the composite interrogation and fluid response signals to produce a combined response;
interpreting the combined response in the composite interrogation and response signals to generate the electrochemical impedance of the fluid; and
storing data representing at least the electrochemical impedance of the fluid.

4. method of claim 3, further comprising measuring the impedance of the fluid in situ.

5. The method of claim 3, wherein the fluid is selected from the group consisting of: fuels, lubricants, coolants and hydraulic fluids.

6. The method of claim 3, wherein the electrochemical impedance is used as an indication of fluid quality.

7. The method of claim 3, wherein interpreting the combined response includes the step of determining both magnitude and phase changes in the response signals.

8. A method for sensing electrochemical impedance of a fluid, comprising:
injecting an interrogation signal into the fluid, wherein the interrogation signal is a broadband voltage signal comprising a plurality of logarithmically-spaced frequencies, and where at least one interrogation signal is created for each frequency range of interest;
detecting, as a response signal, a response to the interrogation signal passed through the fluid;
interpreting a combined response based upon the interrogation and response signal variations to determine the electrochemical impedance; and
storing data representing at least the electrochemical impedance.

9. The method of claim 8, wherein each frequency range spans a decade of frequencies.

10. The method of claim 9, wherein the detecting step further includes:
assessing the response signal indicative of impedance for each decade independently; and
subsequently re-assembling the signal.

11. The method of claim 9, wherein the formula for generating the interrogation signal, $w_D(t)$, includes $$w_D(t) = A \cdot \sum_{n=0}^{N-1} \sin(2\pi \cdot 10^{(D+\frac{n}{N-1})} \cdot t),$$

where A is a scaling value used to obtain the desired magnitude, D defines the decade of frequencies spanned by wD(t), and N is the number of log-spaced signal frequencies.

12. The method of claim 11, wherein the scaling value, A, is selected such that a full dynamic range of a digital to analog converter used to output the interrogation signal, is utilized.

13. The method of claim 3, wherein the impedance of the fluid ($Z_{OIL}$) is calculated as:

$$Z_{OIL}(\omega) = \frac{V_{IN}(\omega t) - V_{OUT}(\omega t - \phi)}{V_{OUT}(\omega t - \phi)} \cdot R - Z_{SENSOR}$$

where $V_{IN}$ is the voltage of the input interrogation signal. $V_{OUT}$ the voltage of the output response signal. R is a reference resistance used in the circuit for measurement of the response signals, and $Z_{SENSOR}$ is a constant to adjust for stray circuit effects.

14. The method of claim 3, wherein interpreting the combined response in the composite interrogation and response signals to generate the electrochemical impedance includes assessing impedance of the fluid over a wide range of frequencies, so as to capture the total impedance response of the system.

15. The method of claim 3, further comprising applying a scaling value to the composite interrogation signal, wherein the scaling value is selected such that a full dynamic range of a digital to analog converter is used to output the composite interrogation signal.

16. The method of claim 3, further including determining a type of fluid contamination.

17. The method of claim 3, further including quantifying at least one level of contamination within the fluid.

18. The method of claim 3, wherein at least one composite interrogation signal is created for each frequency range of interest.

19. The method of claim 18, wherein interpreting the combined response further includes:
assessing the signals indicative of impedance for each frequency range independently; and
subsequently re-assembling the signals.

20. The method of claim 18, wherein the formula for generating the interrogation signal, $w_D(t)$, includes $$w_D(t) = A \cdot \sum_{n=0}^{N-1} \sin\left(2\pi \cdot 10^{\left(D+\frac{n}{N-1}\right)} \cdot t\right),$$

where A is a scaling value used to obtain the desired magnitude, D defines the decade of frequencies spanned by $w_D(t)$, and N is the number of log-spaced signal frequencies.

21. The method of claim 3, wherein a scaling value is applied, and where the scaling value is selected such that a full dynamic range of a digital to analog converter is utilized for each range of the composite interrogation signals to output the composite interrogation signals.

22. The method of claim 3, wherein interpreting the combined response further comprises:
- windowing a portion of the interrogation signal and response signal for a common time interval;
- taking a Fast Fourier Transform of the two signals; and
- locating peaks in a frequency domain at each of the frequencies of a resultant waveform, wherein phase and magnitude signals of input and output voltages for the composite interrogation and fluid response signals are then converted into complex values and the impedance of the fluid is calculated.

* * * * *